(12) United States Patent
Wadekar

(10) Patent No.: US 10,619,091 B2
(45) Date of Patent: Apr. 14, 2020

(54) IMIDAZOLINIUM COMPOUNDS AS DUAL CORROSION INHIBITORS

(71) Applicant: Halliburton Energy Services, Inc., Houston, TX (US)

(72) Inventor: Sushant Dattaram Wadekar, Pune (IN)

(73) Assignee: Halliburton Energy Services, Inc., Houston, TX (US)

(*) Notice: Subject to any disclaimer, the term of this patent is extended or adjusted under 35 U.S.C. 154(b) by 263 days.

(21) Appl. No.: 15/116,448

(22) PCT Filed: May 7, 2014

(86) PCT No.: PCT/US2014/037174
§ 371 (c)(1),
(2) Date: Aug. 3, 2016

(87) PCT Pub. No.: WO2015/171139
PCT Pub. Date: Nov. 12, 2015

(65) Prior Publication Data
US 2017/0009130 A1 Jan. 12, 2017

(51) Int. Cl.
| | |
|---|---|
| *C09K 8/86* | (2006.01) |
| *C09K 8/035* | (2006.01) |
| *C09K 8/60* | (2006.01) |
| *C09K 8/68* | (2006.01) |
| *E21B 41/02* | (2006.01) |

(Continued)

(52) U.S. Cl.
CPC ............. *C09K 8/86* (2013.01); *C07D 233/14* (2013.01); *C09K 8/035* (2013.01); *C09K 8/602* (2013.01); *C09K 8/68* (2013.01); *C09K 8/685* (2013.01); *C09K 8/72* (2013.01); *C09K 8/725* (2013.01); *C09K 8/805* (2013.01); *C09K 8/887* (2013.01); *E21B 10/00* (2013.01); *E21B 21/06* (2013.01); *E21B 41/02* (2013.01); *E21B 43/26* (2013.01); *E21B 43/267* (2013.01); *C09K 2208/30* (2013.01); *C09K 2208/32* (2013.01)

(58) Field of Classification Search
None
See application file for complete search history.

(56) References Cited

U.S. PATENT DOCUMENTS 2,867,279 A * 1/1959 Cocks ..................... C09K 8/86
507/250
7,939,470 B1 5/2011 Wagle et al.
(Continued)

FOREIGN PATENT DOCUMENTS

WO WO-2015171139 A1 11/2015

OTHER PUBLICATIONS

Aiad, Ismail Abdelrhman, "Some Imidazoline Derivatives as Corrosion Inhibitors", J Surfact Deterg (2010), Ch. 13, p. 247-254.
(Continued)

*Primary Examiner* — Jeffrey D Washville
(74) *Attorney, Agent, or Firm* — Chamberlain Hrdlicka

(57) ABSTRACT

A method comprises obtaining or providing a treatment fluid comprising an imidazolinium compound and placing the treatment fluid in a subterranean formation. The imidazolinium compound functions as a viscoelastic surfactant (VES) gelling agent and as a corrosion inhibitor.

29 Claims, 2 Drawing Sheets

(51) Int. Cl.
*C09K 8/80* (2006.01)
*C09K 8/72* (2006.01)
*E21B 43/267* (2006.01)
*E21B 43/26* (2006.01)
*E21B 10/00* (2006.01)
*C07D 233/14* (2006.01)
*C09K 8/88* (2006.01)
*E21B 21/06* (2006.01)

(56) References Cited

U.S. PATENT DOCUMENTS

| | | | |
|---|---|---|---|
| 2008/0176773 A1* | 7/2008 | Wheeler | C09K 8/68 |
| | | | 507/266 |
| 2009/0156432 A1* | 6/2009 | Cassidy | C09K 8/54 |
| | | | 507/205 |
| 2010/0261623 A1 | 10/2010 | Cassidy et al. | |
| 2012/0273200 A1 | 11/2012 | Dakin et al. | |
| 2014/0246198 A1 | 9/2014 | Pandya et al. | |

OTHER PUBLICATIONS

"International Application Serial No. PCT/US2014/037174, International Search Report dated Jan. 30, 2015", 3 pgs.
"International Application Serial No. PCT/US2014/037174, Written Opinion dated Jan. 30, 2015", 8 pgs.

* cited by examiner

IMIDAZOLINIUM COMPOUNDS AS DUAL CORROSION INHIBITORS

PRIORITY APPLICATIONS

This application is a U.S. National Stage Filing under 35 U.S.C. § 371 from International Application No. PCT/US2014/037174, filed on May 7, 2014, and published as WO 2015/171139 on Nov. 12, 2015, which application and publication are incorporated herein by reference in their entirety.

BACKGROUND OF THE INVENTION

Effective diversion of acid is important for efficient treatment of, among other things, carbonate reservoirs. It also increases the depth of penetration of acid into the reservoir. The use of viscoelastic surfactants (VES) based fluids in acid diversion treatment is becoming prevalent due to their non-damaging nature. These fluids develop viscosity by aggregation of surfactants molecules to form micelles. These VES fluids break down easily on dilution or on contact with oil thereby leaving negligible residue in the reservoir.

One drawback of VES fluids is their general incompatibility with corrosion inhibitors. In some instances, corrosion inhibitors interfere in the aggregation of the surfactant molecules in VES fluids and affect at least the gelling properties of VES. Since, rate of corrosion increases at higher temperature, the use of corrosion inhibitors are inevitable in gelled acids for higher temperature applications. There is therefore a need for VES that may be used in the presence of corrosion inhibitors or are corrosion inhibitors themselves.

BRIEF DESCRIPTION OF THE FIGURES

The drawings illustrate generally, by way of example, but not by way of limitation, various embodiments discussed in the present document.

DETAILED DESCRIPTION OF THE INVENTION

Figure 1:
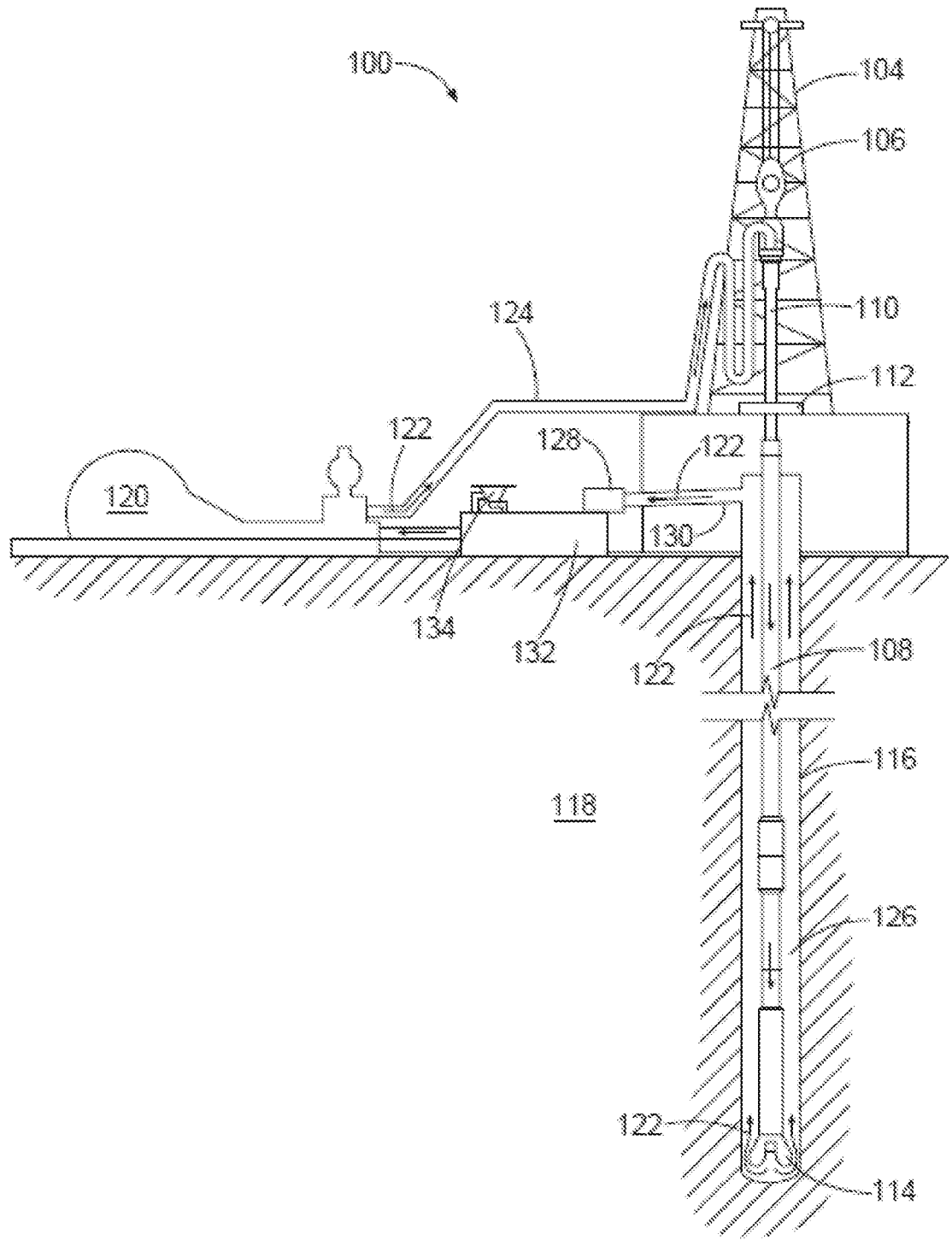
FIG. 1 illustrates a drilling assembly, in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "downhole" as used herein refers to under the surface of the earth, such as a location within or fluidly connected to a wellbore.

As used herein, the term "fluid" refers to liquids and gels, unless otherwise indicated.

As used herein, the term "subterranean material" or "subterranean formation" refers to any material under the surface of the earth, including under the surface of the bottom of the ocean. For example, a subterranean material can be any section of a wellbore and any section of an underground formation in fluid contact with the wellbore, including any materials placed into the wellbore such as cement, drill shafts, liners, tubing, or screens. In some examples, a subterranean material can be any below-ground area that can produce liquid or gaseous petroleum materials, water, or any section below-ground in fluid contact therewith.

Embodiments of the present invention relate to treatment fluids for subterranean formations. More specifically, embodiments of the present invention relate to treatment fluids comprising, among other things, an imidazolinium compound that functions as a VES gelling agent and as a corrosion inhibitor so as to obviate the need for any additional corrosion inhibitors. Embodiments of the present invention also relate to methods of using the treatment fluids in subterranean formations penetrated by wellbores. The treatment fluids of various embodiments of the present invention are suitable for use in, among other applications, acid treatments at elevated temperatures (e.g., temperatures up to 225° F. or higher).

As used herein, the term "treatment fluids" refers generally to any fluid that may be used in a subterranean application in conjunction with a desired function and/or for a desired purpose. The term "treatment fluid" does not imply any particular action by the fluid or any component thereof. As a result, the present compositions can be inexpensive and simple to prepare, using either batch mixing or on-the-fly procedures. In some embodiments, the term "treatment fluids" includes, but is not limited to drilling fluids, stimulation fluids, clean-up fluids, fracturing fluids, spotting fluids, production fluids, completion fluids, remedial treatment fluids, abandonment fluids, acidizing fluids, water control materials, packing fluids or combinations thereof.

As used herein, the term "drilling fluid" refers to fluids, slurries, or muds used in drilling operations downhole, such as the formation of a wellbore.

As used herein, the term "stimulation fluid" refers to fluids or slurries used downhole during stimulation activities of the well that can increase the production of a well, including perforation activities. In some examples, a stimulation fluid can include a fracturing fluid or an acidizing fluid.

As used herein, the term "clean-up fluid" refers to fluids or slurries used downhole during clean-up activities of the well, such as any treatment to remove material obstructing the flow of desired material from the subterranean formation. In one example, a clean-up fluid can be an acidification treatment to remove material formed by one or more perforation treatments. In another example, a clean-up fluid can be used to remove a filter cake.

As used herein, the term "fracturing fluid" refers to fluids or slurries used downhole during fracturing operations.

As used herein, the term "spotting fluid" refers to fluids or slurries used downhole during spotting operations and can be any fluid designed for localized treatment of a downhole region. In one example, a spotting fluid can include a lost circulation material for treatment of a specific section of a wellbore, such as to seal off fractures in a wellbore and prevent sag. In another example, a spotting fluid can include a water control material. In some examples, a spotting fluid can be designed to free a stuck piece of drilling or extraction equipment; can reduce torque and drag with drilling lubricants; prevent differential sticking; promote wellbore stability; and can help to control mud weight.

As used herein, the term "production fluid" refers to fluids or slurries used downhole during the production phase of a well. Production fluids can include downhole treatments designed to maintain or increase the production rate of a well, such as perforation treatments, clean-up treatments or remedial treatments.

As used herein, the term "completion fluid" refers to fluids or slurries used downhole during the completion phase of a well, including cementing compositions.

As used herein, the term "remedial treatment fluid" refers to fluids or slurries used downhole for remedial treatment of a well. Remedial treatments can include treatments designed to increase or maintain the production rate of a well, such as stimulation or clean-up treatments.

As used herein, the term "abandonment fluid" refers to fluids or slurries used downhole during or preceding the abandonment phase of a well.

As used herein, the term "acidizing fluid" or "acidic treatment fluids" refers to fluids or slurries used downhole during acidizing treatments downhole. Acidic treatment fluids can be used during or in preparation for any subterranean operation wherein a fluid may be used. Suitable subterranean operations may include, but are not limited to, acidizing treatments (e.g., matrix acidizing or fracture acidizing), wellbore clean-out treatments, and other operations where a treatment fluid of the present invention may be useful. In a matrix acidizing procedure, for example, an aqueous acidic treatment fluid (e.g., a treatment comprising one or more imidazolinium compounds, an aqueous base fluid, and spent acid) is introduced into a subterranean formation via a wellbore therein under pressure so that the acidic treatment fluid flows into the pore spaces of the formation and reacts with (e.g., dissolves) acid-soluble materials therein. As a result, the pore spaces of that portion of the formation are enlarged, and the permeability of the formation may increase. The flow of hydrocarbons from the formation therefore may be increased because of the increase in formation conductivity caused, among other factors, by dissolution of the formation material.

In fracture acidizing procedures, one or more fractures are produced in the formation(s) and an acidic treatment fluid is introduced into the fracture(s) to etch flow channels therein. Acidic treatment fluids also may be used to clean out wellbores to facilitate the flow of desirable hydrocarbons. Other acidic treatment fluids may be used in diversion processes and wellbore clean-out processes. For example, acidic treatment fluids can be useful in diverting the flow of fluids present within a subterranean formation (e.g., formation fluids and other treatment fluids) to other portions of a formation, for example, by invading higher permeability portions of a formation with a fluid that has high viscosity at low shear rates.

As used herein, the term "cementing fluid" refers to fluids or slurries used during cementing operations of a well. For example, a cementing fluid can include an aqueous mixture including at least one of cement and cement kiln dust. In another example, a cementing fluid can include a curable resinous material, such as a polymer, that is in an at least partially uncured state.

As used herein, the term "fluid control material" (e.g., a "water control material") refers to a solid or liquid material that, by virtue of its viscosification in the flowpaths producing a fluid (e.g., water) alters, reduces or blocks the flow rates of such fluids into the wellbore, such that hydrophobic material can more easily travel to the surface and such that hydrophilic material (including water) can less easily travel to the surface. For example, a fluid control material can be used to treat a well to cause a proportion of a fluid produced, which may include water, to decrease and to cause the proportion of hydrocarbons produced to increase, such as by selectively causing the material to form a viscous plug between water-producing subterranean formations and the wellbore, while still allowing hydrocarbon-producing formations to maintain output.

In some embodiments, the fluid control material mitigates (e.g., reduces, stops or diverts) the flow of fluids (e.g., treatment fluids and water) through a portion of a subterranean formation that is penetrated by the well such that the flow of the fluid into high-permeability portions of the formation is mitigated. For example, in an injection well, it may be desirable to seal off high-permeability portions of a subterranean formation that would otherwise accept most of an injected treatment fluid. By sealing off the high-permeability portions of the subterranean formation, the injected treatment fluid may thus penetrate less permeable portions of the subterranean formation. In other embodiments, the fluid control material helps mitigate the production of undesired fluids (e.g., water) from a well by at least sealing off one or more permeable portions of a treated subterranean formation.

As used herein, the term "packing fluid" refers to fluids or slurries that can be placed in the annular region of a well, between tubing and outer casing above a packer. In various examples, the packer fluid can provide hydrostatic pressure in order to lower differential pressure across a sealing element; lower differential pressure on the wellbore and casing to prevent collapse; and protect metals and elastomers from corrosion.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof.

The term "alkyl" as used herein refers to straight chain and branched alkyl groups and cycloalkyl groups having from 1 to 30 carbon atoms, 10 to 30 carbon atoms, 12 to 18 carbon atoms, 1 to about 20 carbon atoms, 1 to 10 carbons, 1 to 8 carbon atoms 1 to 5 carbon atoms or, in some embodiments, from 1 to 3 carbon atoms. Examples of straight chain alkyl groups include those with from 1 to 8 carbon atoms such as methyl, ethyl, n-propyl, n-butyl, n-pentyl, n-hexyl, n-heptyl, n-octyl groups. Examples of straight chain alkyl groups include those with from 10 to 30 carbon atoms such as n-decyl, n-undecyl, n-dodecyl, n-hexadecyl, n-icosyl, and the like. Examples of branched alkyl groups include, but are not limited to, isopropyl, iso-butyl, sec-butyl, t-butyl, neopentyl, isopentyl, 2,2-dimethylpropyl, and isostearyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 or 12-40 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "heterocyclyl" as used herein refers to aromatic and non-aromatic ring compounds containing 3 or more ring members, of which, one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a C$_2$-heterocyclyl can be a 5-ring with two carbon atoms and three heteroatoms, a 6-ring with two carbon atoms and four heteroatoms and so forth. Likewise a C$_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The terms "halo," "halogen," or "halide" group, as used herein, by themselves or as part of another substituent, mean, unless otherwise stated, a fluorine, chlorine, bromine, or iodine atom.

In general, the treatment fluids of the present invention comprise among other things, an imidazolinium compound that functions as a viscoelastic surfactant (VES) gelling agent and as a corrosion inhibitor. One of many advantages of the treatment fluids of the present invention is that they will be more environmentally friendly, as compared to other corrosion inhibitors and VES known in the art (e.g., SGA-7). Another advantage of the treatment fluids of the present invention is that they do not require the presence of cross-linked polymers. Still another of many advantages of the treatment fluids of the present invention is that they can be single-component treatment fluids where the imidazolinium compound can simultaneously act as a gelling agent and a corrosion inhibitor.

In an embodiment, the treatment fluid is suitable for use, in among other applications, as a gelling agent or as an acid diversion agent in acidizing operations of, e.g., carbonate reservoirs. The imidazolinium compound that functions as a VES gelling agent and/or the treatment fluid comprising the imidazolinium compound(s) of the various embodiments of the present invention, in some embodiments, exhibit viscoelastic behavior (e.g., reversible shear thinning properties).

le;.5qWhile not wishing to be bound by any theory, it is believed that the imidazolinium compounds of the embodiments of the present invention function as corrosion inhibitors for at least metal surfaces at least because they adsorb onto metal surfaces. It is believed that the imidazoline ring of the imidazolinium compounds of the embodiments of the present invention remains flat on a metal surface and protects the metal surface from corrosion. In some embodiments, the imidazolinium compounds of the embodiments of the present invention comprise long alkyl chains (e.g., $C_{10}$-$C_{30}$ alkyl chains and $C_{12}$-$C_{18}$ alkyl chains) It is therefore believed that the long alkyl chains impart water repellency onto a metal surface.

The treatment fluids of the embodiments of the present invention inhibit corrosion such that a significantly reduced corrosion loss is observed in equipment susceptible to corrosion that comes in contact with the treatment fluids. In some embodiments, the corrosion loss observed for equipment susceptible to corrosion that comes in contact with the treatment fluids of the embodiments of the present invention is less than 0.150 lb/ft$^2$ (e.g., 0.001 lb/ft$^2$ to about 0.060 lb/ft$^2$, about 0.010 lb/ft$^2$ to about 0.050 lb/ft$^2$ or about 0.005 lb/ft$^2$ to about 0.050 lb/ft$^2$) over, e.g., a period of two hours at 225° C.

In some embodiments, imidazolinium compounds of the embodiments of the present invention include compounds of the formula (I):

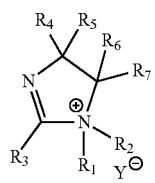

(I)

wherein:

$R_1$ and $R_2$ are each, independently, an optionally substituted $C_1$-$C_{10}$ hydrocarbyl group;

$R_3$ is a $C_{10}$-$C_{30}$ hydrocarbyl group;

$R_4$-$R_7$ are each, independently, H or an optionally substituted $C_1$-$C_{10}$ hydrocarbyl group; and $Y^-$ is a counterion.

In some embodiments, $R_1$ and $R_2$ are each, independently, an optionally substituted $C_1$-$C_5$ hydrocarbyl group; $R_3$ is a $C_{15}$-$C_{25}$ hydrocarbyl group; and $R_4$-$R_7$ are each, independently, H or an optionally substituted $C_1$-$C_{10}$ hydrocarbyl group.

In other embodiments, $R_1$ and $R_2$ are each, independently, an optionally substituted $C_1$-$C_5$ hydrocarbyl group; $R_3$ is a $C_{15}$-$C_{25}$ hydrocarbyl group; and $R_4$-$R_7$ are each H.

In still other embodiments, $R_1$ is an unsubstituted $C_1$-$C_5$ hydrocarbyl group; $R_2$ is a hydroxyl-substituted $C_1$-$C_5$ hydrocarbyl group; $R_3$ is a $C_{15}$-$C_{25}$ hydrocarbyl group; $R_4$-$R_7$ are each, independently, an H or an optionally substituted $C_1$-$C_{10}$ hydrocarbyl group.

In yet other embodiments, $R_1$ and $R_2$ are each, independently, an optionally substituted $C_1$-$C_5$ alkyl group; $R_3$ is a $C_{15}$-$C_{25}$ alkyl group; and $R_4$-$R_7$ are each, independently, H or an optionally substituted $C_1$-$C_{10}$ alkyl group.

In other embodiments, $R_1$ and $R_2$ are each, independently, an optionally substituted $C_1$-$C_5$ alkyl group; $R_3$ is a $C_{15}$-$C_{25}$ alkyl group; and $R_4$-$R_7$ are each H.

In still other embodiments, $R_1$ is an unsubstituted $C_1$-$C_5$ alkyl group; $R_2$ is a hydroxyl-substituted $C_1$-$C_5$ alkyl group; $R_3$ is a $C_{15}$-$C_{25}$ alkyl group; $R_4$-$R_7$ are each, independently, and H or an optionally substituted $C_1$-$C_{10}$ alkyl group.

The counterion in the compounds of the formula (I) can be any suitable counterion including, but not limited to inorganic counterions and organic counterions.

As used herein, the term "inorganic counterion" refers broadly to counterions such as chloride, nitrate, sulfate, phosphate, and the like.

As used herein, the term "organic counterion" refers broadly to a counterion comprising at least one $C_1$-$C_{10}$ hydrocarbyl group. Non-limiting examples of organic counterions include alkoxides ($R_8O^-$, wherein $R_8$ represents a $C_1$-$C_{10}$ hydrocarbyl group, such as phenoxide and t-butoxide), carboxylates ($R_8CO_2^-$, wherein $R_8$ represents a $C_1$-$C_{10}$ hydrocarbyl group, such as acetate, benzoate, and succinate), organic sulfates ($R_8OSO_3^-$, wherein $R_8$ represents a $C_1$-$C_{10}$ hydrocarbyl group, such as ethylsulfate), and organic sulfonates ($R_8SO_3^-$, wherein $R_8$ represents a $C_1$-$C_{10}$ hydrocarbyl group, such as mesylate, triflate, esylate, besylate, and tosylate).

In some embodiments, the compound of the formula (I) is a compound of the formula (II):

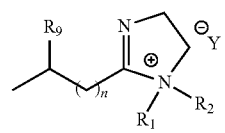

(II)

wherein $R_1$, $R_2$, and $Y^-$ are as defined above; $R_9$ is H or $C_1$-$C_5$ alkyl; and n is an integer from 10 to 25. In some embodiments, in compounds of the formula (II), $R_1$ and $R_2$ are each, independently, an optionally substituted $C_1$-$C_5$ alkyl group. In other embodiments, in compounds of the formula (II), $R_1$ is an unsubstituted $C_1$-$C_5$ alkyl group; and $R_2$ is a hydroxyl-substituted $C_1$-$C_5$ alkyl group.

In other embodiments, the compound of the formula (I) is a compound of the formula (III):

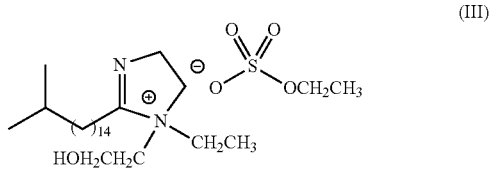

(III)

The compound of the formula (III) is available commercially from Lubrizol Advanced Materials, Inc. (Cleveland, Ohio) under the name Schercoquat™ IIS (also known as "isostearyl imidazolinium ethosulfate") as a mixture of the compound of the formula (III) and propylene glycol (~95% of the compound of formula (III) and ~5% propylene glycol).

In still other embodiments, the compound of the formula (I) is a compound of the formula (IV):

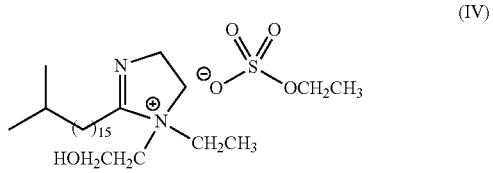

(IV)

The amount of the compounds of the formula (I)-(IV) included in the treatment fluid of the various embodiments of the present invention will depend on many factors, including but not limited to, the metallurgy that the treatment fluid will contact, contact time, and temperature. The amount of the compounds of the formula (I)-(IV) included in the treatment fluid of the various embodiments of the present invention may range from about 0.1% to about 10% by volume (e.g., about 1% to about 10%, about 3% to about 10%, about 3% to about 8%, and about 4% to about 8% by volume) where liquid products are used and from about 0.5% to about 200% by weight (e.g., about 1% to about 150%, about 10% to about 175%, about 50% to about 150%, and about 50% to about 120% by weight) where solid products are used.

In some embodiments, the treatment fluids of the present invention can further comprise other compounds that, like the compounds of the formula (I)-(IV), function as corrosion inhibitors. In some instances, the treatment fluids can also further comprise corrosion inhibitor intensifier compositions. Any of a variety of corrosion inhibitors may be suitable for use in the treatment fluids and methods of the present invention. See, e.g., U.S. Pat. No. 8,058,211, which is incorporated by reference as if fully set forth herein. Examples of suitable corrosion inhibitors include, but are not limited to, cinnamaldehyde compounds, acetylenic compounds, a condensation reaction product, and combinations thereof. While the amount of corrosion inhibitor utilized in the practice of the present invention can vary over a range, the corrosion inhibitor may present in an amount effective to inhibit corrosion by an acid on a metal surfaces to be protected. In certain embodiments, the corrosion inhibitor may be present in an amount of about 0.05% to about 3% by weight of the treatment fluid.

In certain embodiments, corrosion inhibitor compositions useful in the present invention may comprise a cinnamaldehyde compound. The term "cinnamaldehyde compound" as used herein refers to cinnamaldehyde and cinnamaldehyde derivatives. Cinnamaldehyde derivatives may include any compound that may act as a source of cinnamaldehyde in mixtures encountered during use of the corrosion inhibitors. Examples of cinnamaldehyde derivatives suitable for use in the present invention include, but are not limited to, dicinnamaldehyde, p-hydroxycinnamaldehyde, p-methylcinnamaldehyde, p-ethylcinnamaldehyde, p-methoxycinnamaldehyde, p-dimethylaminocinnamaldehyde, p-diethylaminocinnamaldehyde, p-nitrocinnamaldehyde, o-nitrocinnamaldehyde, o-allyloxycinnamaldehyde, 4-(3-propenal)cinnamaldehyde, p-sodium sulfocinnamaldehyde, p-trimethylammoniumcinnamaldehyde sulfate, p-trimethylammoniumcinnamaldehyde, o-methylsulfate, p-thiocyanocinnamaldehyde, p-(S-acetyl)thiocinnamaldehyde, p-(N,N-dimethylcarbamoylthio)cinnamaldehyde, p-chlorocinnamaldehyde, α-methylcinnamaldehyde, .beta.-methylcinnamaldehyde, α-chlorocinnamaldehyde, α-bromocinnamaldehyde, α-butylcinnamaldehyde, α-amylcinnamaldehyde, α-hexylcinnamaldehyde, α-bromo-p-cyanocinnamaldehyde, α-ethyl-p-methylcinnamaldehyde, p-methyl-α-pentylcinnamaldehyde, cinnamaloxime, cinnamonitrile, 5-phenyl-2,4-pentadienal, 7-phenyl-2,4,6-heptatrienal, and mixtures thereof.

Where used, the cinnamaldehyde compound may be present in an amount in the range of about 0.005% to about 5% by weight of the treatment fluid. In certain embodiments, cinnamaldehyde compound may be present in an amount in the range of about 0.02% to about 1% by weight of the treatment fluid.

In certain embodiments, the corrosion inhibitor compositions useful in the present invention may comprise an acetylenic compound. Acetylenic compounds suitable for use in the present invention may include acetylenic alcohols such as, for example, acetylenic compounds having the general formula: $R_{10}C \equiv CCR_{11}R_{12}OH$, wherein $R_{10}$, $R_{11}$, and $R_{12}$ are individually selected from the group consisting of hydrogen, alkyl, and phenyl, as each of the terms is defined herein. Examples of suitable acetylenic alcohols include, but are not limited to, methyl butynol, methyl pentynol, hexynol, ethyl octynol, propargyl alcohol, benzylbutynol, ethynylcyclohexanol, ethoxy acetylenics, propoxy acetylenics, and mixtures thereof. Examples of suitable alcohols include, but are not limited to, hexynol, propargyl alcohol, methyl butynol, ethyl octynol, propargyl alcohol ethoxylate (e.g., Golpanol PME), propargyl alcohol propoxylate (e.g., Golpanol PAP), and mixtures thereof. When used, the acetylenic compound may be present in an amount of about 0.01% to about 10% by weight of the treatment fluid. In certain embodiments, the acetylenic compound may be present in an amount of about 0.1% to about 1.5% by weight of the treatment fluid.

In certain embodiments, corrosion inhibitor compositions useful in the present invention may optionally comprise a condensation reaction product of the reaction of (i) a compound having at least one reactive hydrogen atom and having no groups reactive under the conditions of reaction other than hydrogen; (ii) a carbonyl compound having at least one hydrogen atom on the carbon atom adjacent to the carbonyl group; (iii) an aldehyde; (iv) a fatty compound; and an acid source which is admixed with a source of antimony ions. See, e.g., U.S. Pat. No. 5,366,643, which is incorporated by reference as if fully set forth herein.

Other suitable corrosion inhibitors include fluorinated surfactants, quaternary derivatives of heterocyclic nitrogen bases, and corrosion inhibitors described in U.S. Pat. No. 7,846,879, which is incorporated by reference as if fully set forth herein.

Still other corrosion inhibitors include Mannich condensation products (e.g., those formed by reacting an aldehyde, a carbonyl containing compound and a nitrogen containing compound), unsaturated carbonyl compounds, unsaturated ether compounds, formamide, formic acid, formates, other sources of carbonyl, iodides, terpenes, and aromatic hydrocarbons, coffee, tobacco, gelatin, quaternary derivatives of halomethylated aromatic compounds, formamides, combinations of such compounds used in conjunction with iodine, quaternary ammonium compounds, and combinations thereof.

Examples of commercially-available corrosion inhibitors include MSA II™ corrosion inhibitor, MSA III™, HAI-404M™, HAI-81M™, HAI-85M™, HAI-202, HAI-OS, HAI-GE, and FDP-S692-03 corrosion inhibitors, all of which are available from Halliburton Energy Services. See, e.g., U.S. Pat. No. 7,727,937, which is incorporated by reference as if fully set forth herein.

In certain embodiments, a corrosion inhibitor activator may be included. Examples of corrosion inhibitor activators that may be used include, but are not limited to, cuprous iodide; cuprous chloride; antimony compounds such as antimony oxides, antimony halides, antimony tartrate, antimony citrate, alkali metal salts of antimony tartrate and antimony citrate, alkali metal salts of pyroantimonate and antimony adducts of ethylene glycol; bismuth compounds such as bismuth oxides, bismuth halides, bismuth tartrate, bismuth citrate, alkali metal salts of bismuth tartrate and bismuth citrate; iodine; iodide compounds; formic acid; and mixtures of the foregoing activators such as a mixture of formic acid and potassium iodide.

As mentioned herein, in some embodiments, the treatment fluids of the present invention can further comprise corrosion inhibitors and, in some instances, corrosion inhibitor intensifier compositions. As used herein, the term "corrosion inhibitor intensifier compositions" refers to compositions that are capable of enhancing the performance of a selected corrosion inhibitor. Suitable corrosion inhibitor intensifier compositions comprise, e.g., formic acid, potassium iodide, antimony-based intensifiers, and cuprous iodide.

Examples of commercially-available corrosion inhibitor intensifier compositions include HII-500™, HII-500M™, HII-124B, HII-124C™, and HII-124F™ corrosion inhibitor intensifier compositions, all of which are available from Halliburton Energy Services. See, e.g., U.S. Pat. No. 7,727,937, which is incorporated by reference as if fully set forth herein.

The amount of a corrosion inhibitor included in the treatment fluid of the various embodiments of the present invention will depend on many factors, including but not limited to, the metallurgy that the treatment fluid will contact, contact time, and temperature. Where included, the amount of a corrosion inhibitor may range from about 0.1% to about 3% by volume where liquid products are used and from about 0.5% to about 200% by weight where solid products are used.

In some embodiments, the treatment fluids of the embodiments of the present invention do not comprise any additional corrosion inhibitors in addition to the compounds of the formula (I)-(IV).

In some embodiments, the treatment fluids of the various embodiments of the present invention comprise a suitable aqueous base fluid. The aqueous base fluid used in the treatment fluids of the embodiments of the present invention comprises one or more aqueous fluids. For example, the aqueous base fluid may include, but is not limited to, seawater, produced water, flowback water, fresh water, salt-water (e.g., water containing one or more salts dissolved therein), brine (e.g., saturated saltwater), weighted brine (e.g., an aqueous solution of sodium bromide, calcium bromide, zinc bromide and the like), or any combination thereof. Generally, the aqueous fluid may be from any source, provided that it does not contain components that might adversely affect the stability and/or performance of the treatment fluids of the embodiments of the present invention. In certain embodiments, the aqueous base fluids comprise water-miscible solvents such alcohols (e.g., isopropanol), alcohol ethers (e.g., ethylene glycol methyl ether, ethyleneglycol butyl ether or combinations thereof) or ketones (e.g., acetone, methyl ethyl ketone or combinations thereof)

In some embodiments, the treatment fluids can include any suitable amount of any suitable material used in a downhole fluid. For example, the treatment fluid can include water, saline, aqueous base, oil, organic solvent, synthetic fluid oil phase, aqueous solution, alcohol or polyol, cellulose, starch, alkalinity control agents, acidity control agents, density control agents, density modifiers, emulsifiers, dispersants, polymeric stabilizers, crosslinking agents, polyacrylamide, a polymer or combination of polymers, antioxidants, heat stabilizers, foam control agents, solvents, diluents, rheology modifier, oil-wetting agents, surfactants, corrosion inhibitors, gases, lost circulation materials, filtration control additives, salts, fibers, thixotropic additives, crosslinkers, rheology modifiers, pH modifiers, chelating agents, scale inhibitors, enzymes, resins, water control materials, markers, hydrate inhibitors, clay stabilizers, bactericides, salt substitutes (such as tetramethyl ammonium chloride), relative permeability modifiers (such as HPT-1™ chemical additive available from Halliburton Energy Services), sulfide scavengers, fibers, nanoparticles, consolidating agents (such as resins and/or tackifiers), surfactants, breakers, fluid loss control additives, asphaltene inhibitors, paraffin inhibitors, salts, bactericides, chelants, foamers, defoamers, emulsifiers, demulsifiers, iron control agents, sulfide cracking agents, particulate diverters, gas phase, carbon dioxide, nitrogen, synthetic polymers, friction reducers or a combination thereof.

In some embodiments, the treatment fluids of the present invention may comprise particulates, such as proppant particulates (e.g., resin-coated proppant) or gravel particulates. Particulates suitable for use in the present invention may comprise any material suitable for use in subterranean operations. Suitable materials for these particulates include, but are not limited to, sand, bauxite, ceramic materials, glass materials, polymer materials, Teflon® materials, nut shell pieces, cured resinous particulates comprising nut shell pieces, seed shell pieces, cured resinous particulates comprising seed shell pieces, fruit pit pieces, cured resinous particulates comprising fruit pit pieces, wood, composite particulates, and combinations thereof. Suitable composite particulates may comprise a binder and a filler material wherein suitable filler materials include silica, alumina, fumed carbon, carbon black, graphite, mica, titanium dioxide, meta-silicate, calcium silicate, kaolin, talc, zirconia, boron, fly ash, hollow glass microspheres, solid glass, and combinations thereof. The particulate size generally may range from about 2 mesh to about 400 mesh or smaller on the U.S. Sieve Series; however, in certain circumstances, other sizes may be desired and will be entirely suitable for practice of the present invention. In particular embodiments, preferred particulates size distribution ranges are one or more of 6/12, 8/16, 12/20, 16/30, 20/40, 30/50, 40/60, 40/70, or 50/70 mesh. Also, mixtures of particulates may be used having different particle size distribution ranges to enhance the packed volume of the proppant particulates within the fracture. It should be understood that the term "particulate," as used in this disclosure, includes all known shapes of materials, including substantially spherical materials, fibrous materials, polygonal materials (such as cubic materials), and mixtures thereof. Moreover, fibrous materials, that may or may not be used to bear the pressure of a closed fracture, may be included in certain embodiments of the present invention. In certain embodiments, the particulates may be present in the treatment fluids of the present invention in an amount in the range of from about 0.5 pounds per gallon ("ppg") to about 30 ppg by volume of the treatment fluid. In certain other embodiments, the proppant is about 1 wt % to about 90 wt % of the treatment fluid, e.g., about 5 wt % to about 70 wt % of the treatment fluid.

In some embodiments, the treatment fluids of the various embodiments of the present invention further comprise spent acid, such as spent acids derived from hydrochloric acid, hydrofluoric acid, acetic acid, formic acid, citric acid, lactic acid, glycolic acid, sulfamic acid, and the like and combinations thereof.

The treatment fluids of the various embodiments of the present invention have a viscosity of about 30 cP to about 150 cP at a shear rate of about 20 $s^{-1}$ to about 200 $s^{-1}$ at about 225° F. in the presence of spent acid (e.g., from about 10% to about 75% spent acid, about 10% to about 50% spent acid, about 10% to about 30% spent acid, and about 15% to about 30% spent acid). In some instances, the term "spent acid," as used herein, refers to an acid composition comprising $CaCO_3$ or $CaMg(CO_3)_2$ as a result of an acid coming in contact with a carbonate reservoir during a drilling operation. When the treatment fluids of the various embodiments of the present invention come in contact with the spent acid, they develop a viscosity of about 20 cP to about 150 cP (e.g., about 30 cP to about 150 cP, about 20 cP to about 100 cP, about 50 cP to about 125 cP, about 30 cP to about 90 cP or about 20 cP to about 90 cP) at a shear rate of about 20 $s^{-1}$ to about 200 $s^{-1}$ (e.g., about 20 $s^{-1}$ to about 180 $s^{-1}$, about 40 $s^{-1}$ to about 180 $s^{-1}$, about 40 $s^{-1}$ to about 100 $s^{-1}$, about 80 $s^{-1}$ to about 170 $s^{-1}$ or about 40 $s^{-1}$ to about 170 $s^{-1}$) at about 225° F. (e.g., about 150° F. to about 300° F., about 150° F. to about 250° F., about 200° F. to about 300° F. or about 200° F. to about 275° F.).

In some embodiments, the treatment fluids of the various embodiments of the present invention can further comprise one or more gelling agents, in addition to the compounds of the formula (I)-(IV). Gelling agents include, but are not limited to, alginate, chitosan, curdlan, dextran, emulsan, a galactoglucopolysaccharide, gellan, glucuronan, N-acetyl-heparosan, hyaluronic acid, indicant, kefiran, lentinan, levan, mauran, pullulan, scleroglucan, schizophyllan, stewartan, succinoglycan, xanthan gum, xylane, welan, starch, tamarind, tragacanth, guar gum, derivatized guar, gum ghatti, gum arabic, locust bean gum, diutan gum, cellulose, hydroxyethylcellulose, hemicellulose, carboxymethyl cellulose, hydroxyethyl cellulose, carboxymethyl hydroxyethyl cellulose, hydroxypropyl cellulose, methyl hydroxyl ethyl cellulose, guar, hydroxypropyl guar, carboxy methyl guar, carboxymethyl hydroxylpropyl guar or combinations thereof.

When gelling agents are present, the treatment fluids of the various embodiments of the present invention can further comprise crosslinking agents. Examples of suitable crosslinking agents include, but are not limited to borate ions and zirconium ions. These ions may be provided by providing any compound that is capable of producing one or more of these ions. Examples of such compounds include, but are not limited to, boric acid, disodium octaborate tetrahydrate, sodium diborate, pentaborates, ulexite, colemanite, zirconium oxychloride, chelates of zirconium, derivatives thereof, and combinations thereof. Suitable crosslinking agents also include titanium based compounds such as titanium oxychloride or organic titanates, such as titanium chloride and triethyl amine complexes, and aluminium based compounds, such as aluminium acetate, organo aluminium complexes, and the like. The crosslinking agent, when present, may be present in the treatment fluid in an amount in the range of from about 0.01 percent to about 1.5 percent by weight of the treatment fluid, e.g., 0.1 percent to about 0.5 percent by weight, from about 0.15 percent to about 0.35 percent by weight, from about 0.2 percent to about 0.3 percent by weight or from about 0.15 to about 0.3 percent by weight of the treatment fluid.

In some embodiments, the treatment fluids of the various embodiments of the present invention can further comprise breakers capable of reducing the viscosity of the treatment fluid at a desired time. Examples of such breakers that may be suitable for the acidic treatment fluids of the present invention include, but are not limited to, sodium chlorite, hypochlorites, perborates, persulfates, peroxides (including organic peroxides), enzymes, derivatives thereof, and combinations thereof. Other suitable breakers may include suitable acids. Examples of peroxides that may be suitable include tert-butyl hydroperoxide and tert-amyl hydroperoxide. A breaker may be included in a treatment fluid of the present invention in an amount and form sufficient to achieve the desired viscosity reduction at a desired time. The breaker may be formulated to provide a delayed break, if desired. For example, a suitable breaker may be encapsulated if desired. Suitable encapsulation methods are known to those skilled in the art. One suitable encapsulation method that may be used involves coating the breaker(s) with a material that will degrade when placed downhole so as to release the breaker at the appropriate time. Coating materials that may be suitable include, but are not limited to, polymeric materials that will degrade when downhole.

Optionally, a treatment fluid of the present invention may contain an activator or a retarder to, among other things, optimize the rate at which the fluid is "broken" (e.g., the viscosity of the fluid is reduced). Any known activator or retarder that is compatible with the fluid and the components thereof is suitable for use in the present invention. Examples of such activators that may be suitable include, but are not limited to, acid generating materials, chelated iron, copper, cobalt, reducing sugars, derivatives thereof, and combinations thereof. Examples of retarders that may be suitable include sodium thiosulfate and diethylene triamine. In some embodiments, the sodium thiosulfate may be used in a range of from about 1 to about 100 lbs per 1000 gallons of acidic treatment fluid. A preferred concentration range may be from about 5 to about 20 lbs per 1000 gallons. A person of ordinary skill with the benefit of this disclosure will be able to identify a suitable activator or retarder and the proper concentration of such activator or retarder for a given application.

One advantage of the treatment fluids of the present invention is that they are stable at temperatures above about 200° F. (e.g., above about 220° F., above about 250° F. or above about 300° F., from about 200° F. to about 300° F., from about 200° F. to about 350° F., from about 200° F. to about 250° F., from about 220° F. to about 350° F., from about 250° F. to about 350° F. or from about 300° F. to about 350° F.).

In some embodiments, the treatment fluids of the present invention may be used at temperatures ranging from about 70° F. to about 250° F., e.g., from about 100° F. to about 250° F. or from about 150° F. to about 250° F.

The treatment fluids disclosed herein may directly or indirectly affect one or more components or pieces of equipment associated with the preparation, delivery, recapture, recycling, reuse, and/or disposal of the disclosed treatment fluids. For example, and with reference to FIG. 1, the disclosed treatment fluid may directly or indirectly affect one or more components or pieces of equipment associated with a wellbore drilling assembly 100, according to one or more embodiments. It should be noted that while FIG. 1 generally depicts a land-based drilling assembly, those skilled in the art will readily recognize that the principles described herein are equally applicable to subsea drilling operations that employ floating or sea-based platforms and rigs, without departing from the scope of the disclosure.

As illustrated, the drilling assembly 100 may include a drilling platform 102 that supports a derrick 104 having a traveling block 106 for raising and lowering a drill string 108. The drill string 108 may include, but is not limited to, drill pipe and coiled tubing, as generally known to those skilled in the art. A kelly 110 supports the drill string 108 as it is lowered through a rotary table 112. A drill bit 114 is attached to the distal end of the drill string 108 and is driven either by a downhole motor and/or via rotation of the drill string 108 from the well surface. As the bit 114 rotates, it creates a wellbore 116 that penetrates various subterranean formations 118.

A pump 120 (e.g., a mud pump) circulates drilling fluid 122 through a feed pipe 124 and to the kelly 110, which conveys the drilling fluid 122 downhole through the interior of the drill string 108 and through one or more orifices in the drill bit 114. The drilling fluid 122 is then circulated back to the surface via an annulus 126 defined between the drill string 108 and the walls of the wellbore 116. At the surface, the recirculated or spent drilling fluid 122 exits the annulus 126 and may be conveyed to one or more fluid processing unit(s) 128 via an interconnecting flow line 130. After passing through the fluid processing unit(s) 128, a "cleaned" drilling fluid 122 is deposited into a nearby retention pit 132 (e.g., a mud pit). While illustrated as being arranged at the outlet of the wellbore 116 via the annulus 126, those skilled in the art will readily appreciate that the fluid processing unit(s) 128 may be arranged at any other location in the drilling assembly 100 to facilitate its proper function, without departing from the scope of the disclosure.

The components of the treatment fluid may be added to, among other things, a drilling fluid 122 via a mixing hopper 134 communicably coupled to or otherwise in fluid communication with the retention pit 132. The mixing hopper 134 may include, but is not limited to, mixers and related mixing equipment known to those skilled in the art. In other embodiments, however, the treatment fluid may be added to, among other things, a drilling fluid 122 at any other location in the drilling assembly 100. In at least one embodiment, for example, there could be more than one retention pit 132, such as multiple retention pits 132 in series. Moreover, the retention pit 132 may be representative of one or more fluid storage facilities and/or units where the treatment fluid may be stored, reconditioned, and/or regulated until added to a drilling fluid 122.

As mentioned above, the treatment fluid may directly or indirectly affect the components and equipment of the drilling assembly 100. For example, the treatment fluid may directly or indirectly affect the fluid processing unit(s) 128, which may include, but is not limited to, one or more of a shaker (e.g., shale shaker), a centrifuge, a hydrocyclone, a separator (including magnetic and electrical separators), a desilter, a desander, a separator, a filter (e.g., diatomaceous earth filters), a heat exchanger, or any fluid reclamation equipment. The fluid processing unit(s) 128 may further include one or more sensors, gauges, pumps, compressors, and the like used to store, monitor, regulate, and/or recondition the treatment fluid.

The treatment fluid may directly or indirectly affect the pump 120, which representatively includes any conduits, pipelines, trucks, tubulars, and/or pipes used to fluidically convey the treatment fluid downhole, any pumps, compressors, or motors (e.g., topside or downhole) used to drive the composition into motion, any valves or related joints used to regulate the pressure or flow rate of the composition, and any sensors (e.g., pressure, temperature, flow rate, and the like), gauges, and/or combinations thereof, and the like. The treatment fluid may also directly or indirectly affect the mixing hopper 134 and the retention pit 132 and their assorted variations.

The treatment fluid may also directly or indirectly affect the various downhole equipment and tools that may come into contact with the treatment fluid such as, but not limited to, the drill string 108, any floats, drill collars, mud motors, downhole motors, and/or pumps associated with the drill string 108, and any measurement while drilling (MWD)/logging while drilling (LWD) tools and related telemetry equipment, sensors, or distributed sensors associated with the drill string 108. The treatment fluid may also directly or indirectly affect any downhole heat exchangers, valves and corresponding actuation devices, tool seals, packers and other wellbore isolation devices or components, and the like associated with the wellbore 116. The treatment fluid may also directly or indirectly affect the drill bit 114, which may include, but is not limited to, roller cone bits, polycrystalline diamond compact (PDC) bits, natural diamond bits, any hole openers, reamers, coring bits, and the like.

While not specifically illustrated herein, the treatment fluid may also directly or indirectly affect any transport or delivery equipment used to convey the treatment fluid to the drilling assembly 100 such as, for example, any transport vessels, conduits, pipelines, trucks, tubulars, and/or pipes used to fluidically move the treatment fluid from one location to another, any pumps, compressors, or motors used to drive the composition into motion, any valves or related joints used to regulate the pressure or flow rate of the composition, and any sensors (e.g., pressure and temperature), gauges, and/or combinations thereof, and the like.

In various embodiments, the present invention provides a system. The system can be any suitable system that can use or that can be generated by use of the treatment fluid described herein, or that can perform or be generated by performance of a method for using the treatment fluid described herein. The system can include a composition including the treatment fluid. The system can also include a subterranean formation including the treatment fluid therein. In some embodiments, the treatment fluid in the system can also include at least one of an aqueous liquid, a downhole fluid, and a proppant.

In some embodiments, the system can include a tubular disposed in a wellbore. The system can include a pump configured to pump the composition downhole through the tubular and into the subterranean formation. In some embodiments, the system can include a subterranean formation including the composition therein.

In some embodiments, the system can include a drillstring disposed in a wellbore. The drillstring can include a drill bit at a downhole end of the drillstring. The system can include an annulus between the drillstring and the wellbore. The system can include a pump configured to circulate the composition through the drill string, through the drill bit, and back above-surface through the annulus. The system can further include a fluid processing unit configured to process the composition exiting the annulus to generate a cleaned drilling fluid for recirculation through the wellbore.

In various embodiments, the present invention provides an apparatus. The apparatus can be any suitable apparatus that can use or that can be generated by use of the treatment fluid described herein in a subterranean formation, or that can perform or be generated by performance of a method for using the method for using the treatment fluid described herein.

Various embodiments provide systems and apparatus configured for delivering the treatment fluid described herein to a downhole location and for using the composition therein. In various embodiments, the systems can include a pump fluidly coupled to a tubular (e.g., any suitable type of oilfield pipe, such as pipeline, drill pipe, production tubing, and the like), the tubular containing a treatment fluid described herein.

The pump can be a high pressure pump in some embodiments. As used herein, the term "high pressure pump" will refer to a pump that is capable of delivering a fluid downhole at a pressure of about 1000 psi or greater. A high pressure pump can be used when it is desired to introduce the composition to a subterranean formation at or above a fracture gradient of the subterranean formation, but it can also be used in cases where fracturing is not desired. In some embodiments, the high pressure pump can be capable of fluidly conveying particulate matter, such as proppant particulates, into the subterranean formation. Suitable high pressure pumps will be known to one having ordinary skill in the art and can include, but are not limited to, floating piston pumps and positive displacement pumps.

In other embodiments, the pump can be a low pressure pump. As used herein, the term "low pressure pump" will refer to a pump that operates at a pressure of about 1000 psi or less. In some embodiments, a low pressure pump can be fluidly coupled to a high pressure pump that is fluidly coupled to the tubular. That is, in such embodiments, the low pressure pump can be configured to convey the composition to the high pressure pump. In such embodiments, the low pressure pump can "step up" the pressure of the composition before it reaches the high pressure pump.

In some embodiments, the systems or apparatuses described herein can further include a mixing tank that is upstream of the pump and in which the treatment fluid is formulated. In various embodiments, the pump (e.g., a low pressure pump, a high pressure pump, or a combination thereof) can convey the composition from the mixing tank or other source of the composition to the tubular. In other embodiments, however, the composition can be formulated offsite and transported to a worksite, in which case the composition can be introduced to the tubular via the pump directly from its shipping container (e.g., a truck, a railcar, a barge, or the like) or from a transport pipeline. In either case, the composition can be drawn into the pump, elevated to an appropriate pressure, and then introduced into the tubular for delivery downhole.

Figure 2:
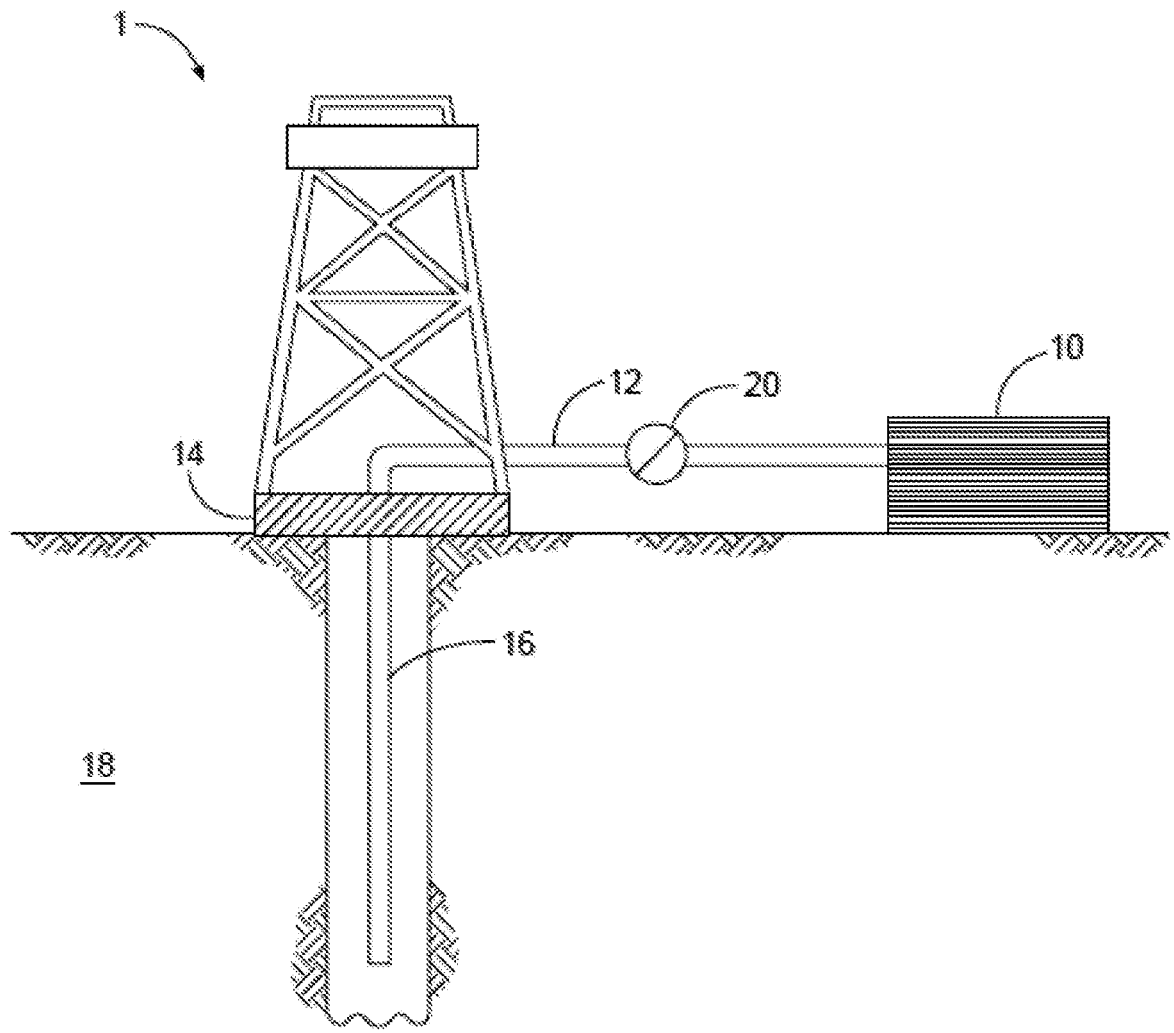
FIG. 2 illustrates a system or apparatus for delivering a composition to a subterranean formation, in accordance with various embodiments.

FIG. 2 shows an illustrative schematic of systems and apparatuses that can deliver treatment fluids of the present invention to a downhole location, according to one or more embodiments. It should be noted that while FIG. 2 generally depicts a land-based system or apparatus, it is to be recognized that like systems and apparatuses can be operated in subsea locations as well. Embodiments of the present invention can have a different scale than that depicted in FIG. 2. As depicted in FIG. 2, system or apparatus 1 can include mixing tank 10, in which an embodiment of the composition can be formulated. The composition can be conveyed via line 12 to wellhead 14, where the composition enters tubular 16, with tubular 16 extending from wellhead 14 into subterranean formation 18. Upon being ejected from tubular 16, the composition can subsequently penetrate into subterranean formation 18. Pump 20 can be configured to raise the pressure of the composition to a desired degree before its introduction into tubular 16. It is to be recognized that system or apparatus 1 is merely exemplary in nature and various additional components can be present that have not necessarily been depicted in FIG. 2 in the interest of clarity. Non-limiting additional components that can be present include, but are not limited to, supply hoppers, valves, condensers, adapters, joints, gauges, sensors, compressors, pressure controllers, pressure sensors, flow rate controllers, flow rate sensors, temperature sensors, and the like.

Although not depicted in FIG. 2, at least part of the composition can, in some embodiments, flow back to wellhead 14 and exit subterranean formation 18. The composition that flows back can be substantially diminished in the concentration of the treatment fluid. In some embodiments, the composition that has flowed back to wellhead 14 can subsequently be recovered, and in some examples reformulated, and recirculated to subterranean formation 18.

It is also to be recognized that the disclosed treatment fluid can also directly or indirectly affect the various downhole equipment and tools that can come into contact with the composition during operation. Such equipment and tools can include, but are not limited to, wellbore casing, wellbore liner, completion string, insert strings, drill string, coiled tubing, slickline, wireline, drill pipe, drill collars, mud motors, downhole motors and/or pumps, surface-mounted motors and/or pumps, centralizers, turbolizers, scratchers, floats (e.g., shoes, collars, valves, and the like), logging tools and related telemetry equipment, actuators (e.g., electromechanical devices, hydromechanical devices, and the like), sliding sleeves, production sleeves, plugs, screens, filters, flow control devices (e.g., inflow control devices, autonomous inflow control devices, outflow control devices, and the like), couplings (e.g., electro-hydraulic wet connect, dry connect, inductive coupler, and the like), control lines (e.g., electrical, fiber optic, hydraulic, and the like), surveillance lines, drill bits and reamers, sensors or distributed sensors, downhole heat exchangers, valves and corresponding actuation devices, tool seals, packers, cement plugs, bridge plugs, and other wellbore isolation devices or components, and the like. Any of these components can be included in the systems and apparatuses generally described above and depicted in FIG. 2.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

EXAMPLES

The present invention can be better understood by reference to the following example which is offered by way of illustration. The present invention is not limited to the example given herein.

Example 1

Table 1, below, demonstrates the rheology of a treatment fluid comprising 7% Schercoquat™ IIS in simulated 15% spent acid fluid. The treatment fluid showed viscosity above 50 cP at 225° F. and 40 sec$^{-1}$.

The 7% Schercoquat™ IIS in simulated 15% spent acid fluid can be prepared by any suitable method known in the art. In some examples, the 7% Schercoquat™ IIS in simulated 15% spent acid fluid can be prepared by combining 11.4 g $CaCl_2$, 9.8 g $MgCl_2$, 82.2 mL water, 6.5 mL of Schercoquat™ IIS, and adjusting the pH 4 with hydrochloric acid to simulate spent acid on dolomite.

The same treatment fluid also passed the corrosion test in live acid (15% HCl) at 225° F. for two hours, as shown on Table 2. The corrosion test is carried out in high pressure-high temperature (HPHT) corrosion autoclaves. The treatment fluid was able to inhibit the corrosion by about four times lower as compared to a control at 225° F. This indicated that treatment fluids comprising Schercoquat™ IIS act as an effective acid diversion fluids and have corrosion inhibiting properties.

TABLE 1

Viscosity of Schercoquat ™ IIS based treatment fluid at 225° F. in simulated 15% spent acid (pH adjusted to 4.0)

| Fluid System | T (° F.) | Viscosity (cP) | | |
|---|---|---|---|---|
| | | 40 s$^{-1}$ | 100 s$^{-1}$ | 170 s$^{-1}$ |
| Schercoquat ™ IIS (70 gal/Mgal) | 225 | 83 | 34 | 20 |

TABLE 2

Corrosion test results in live acid (15% HCl) using P-110 coupons carried out in HPHT autoclaves under nitrogen pressure of 1000 psi

| Test No. | T (° F.) | Time (h) | Corrosion inhibitor | Corrosion inhibitor intensifier | Corrosion loss (lb/ft$^2$) |
|---|---|---|---|---|---|
| 1 | 225 | 2 | None | — | 0.164 |
| 2 | 225 | 2 | Schercoquat ™ IIS (7%) | — | 0.046 |

The following embodiments are provided, the numbering of which is not to be construed as designating levels of importance:

Embodiment 1 relates to a method comprising:
obtaining or providing a treatment fluid comprising a compound of the formula (I):

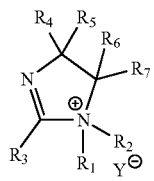

wherein:
$R_1$ and $R_2$ are each, independently, an optionally substituted $C_1$-$C_{10}$ hydrocarbyl group;
$R_3$ is a $C_{10}$-$C_{30}$ hydrocarbyl group;
$R_4$-$R_7$ are each, independently, H or an optionally substituted $C_1$-$C_{10}$ hydrocarbyl group; and
$Y^-$ is a counterion; and
placing the treatment fluid in a subterranean formation.

Embodiment 2 relates to the method of Embodiment 1, wherein the treatment fluid has a viscosity of about 30 cP to about 150 cP at a shear rate of about 20 s$^{-1}$ to about 200 s$^{-1}$ at about 225° F. in the presence of spent acid.

Embodiment 3 relates to the method of Embodiments 1-2, wherein $R_1$ and $R_2$ are each, independently, an optionally substituted $C_1$-$C_5$ hydrocarbyl group; $R_3$ is a $C_{15}$-$C_{25}$ hydrocarbyl group; and $R_4$-$R_7$ are each, independently, H or an optionally substituted $C_1$-$C_{10}$ hydrocarbyl group.

Embodiment 4 relates to the method of Embodiments 1-3, wherein $R_1$ and $R_2$ are each, independently, an optionally substituted $C_1$-$C_5$ hydrocarbyl group; $R_3$ is a $C_{15}$-$C_{25}$ hydrocarbyl group; and $R_4$-$R_7$ are each H.

Embodiment 5 relates to the method of Embodiments 1-4, wherein $R_1$ is an unsubstituted $C_1$-$C_5$ hydrocarbyl group; $R_2$ is a hydroxyl-substituted $C_1$-$C_5$ hydrocarbyl group; $R_3$ is a $C_{15}$-$C_{25}$ hydrocarbyl group; $R_4$-$R_7$ are each, independently, an H or an optionally substituted $C_1$-$C_{10}$ hydrocarbyl group.

Embodiment 6 relates to the method of Embodiments 1-5, wherein $Y^-$ is an organic counterion.

Embodiment 7 relates to the method of Embodiments 1-6, wherein the organic counterion is selected from the group consisting of an alkoxide, a carboxylate, an organic sulfate, and an organic sulfonate.

Embodiment 8 relates to the method of Embodiments 1-7, wherein the organic counterion is an organic sulfate.

Embodiment 9 relates to the method of Embodiments 1-8, wherein the organic counterion is an organic sulfate of the formula $R_8OSO_3^-$, wherein $R_8$ represents a $C_1$-$C_{10}$ hydrocarbyl group.

Embodiment 10 relates to the method of Embodiments 1-9, wherein the compound of the formula (I) is a compound of the formula (II):

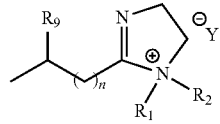

wherein $R_9$ is H or $C_1$-$C_5$ alkyl and n is an integer from 10 to 25.

Embodiment 11 relates to the method of Embodiments 1-10, wherein the compound of the formula (I) is a compound of the formula (III):

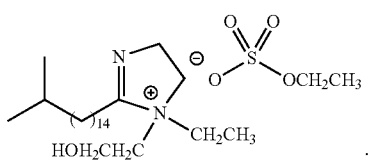

Embodiment 12 relates to the method of Embodiments 1-11, wherein the treatment fluid exhibits viscoelastic behavior.

Embodiment 13 relates to the method of Embodiments 1-12, wherein the treatment fluid further comprises spent acid.

Embodiment 14 relates to the method of Embodiments 1-13, wherein the treatment fluid further comprises a gelling agent and a crosslinking agent.

Embodiment 15 relates to the method of Embodiment 14, wherein the gelling agent comprises alginate, chitosan, curdlan, dextran, emulsan, a galactoglucopolysaccharide, gellan, glucuronan, N-acetyl-heparosan, hyaluronic acid, indictan, kefiran, lentinan, levan, mauran, pullulan, scleroglucan, schizophyllan, stewartan, succinoglycan, xanthan gum, xylane, welan, starch, tamarind, tragacanth, guar gum, derivatized guar, gum ghatti, gum arabic, locust bean gum, diutan gum, cellulose, hydroxyethylcellulose, hemicellulose, carboxymethyl cellulose, hydroxyethyl cellulose, carboxymethyl hydroxyethyl cellulose, hydroxypropyl cellulose, methyl hydroxyl ethyl cellulose, guar, hydroxypropyl guar, carboxy methyl guar, carboxymethyl hydroxylpropyl guar or combinations thereof.

Embodiment 16 relates to the method of Embodiment 14, wherein the crosslinking agent comprises boric acid, disodium octaborate tetrahydrate, sodium diborate, pentaborates, ulexite, colemanite, zirconium oxychloride, chelates of zirconium, derivatives thereof or combinations thereof.

Embodiment 17 relates to the method of Embodiments 1-16, wherein the treatment fluid further comprises a corrosion inhibitor (e.g., a corrosion inhibitor in addition to the compound of formula (I), which compound functions as a viscoelastic surfactant (VES) gelling agent and as a corrosion inhibitor).

Embodiment 18 relates to the method of Embodiments 1-17, wherein the treatment fluid further comprises a corrosion inhibitor intensifier composition.

Embodiment 19 relates to the method of Embodiments 1-18, wherein the obtaining or providing of the composition occurs above-surface.

Embodiment 20 relates to the method of Embodiments 1-18, wherein the obtaining or providing of the composition occurs downhole.

Embodiment 21 relates to the method of Embodiments 1-20, wherein the method is a method of drilling the subterranean formation.

Embodiment 22 relates to the method of Embodiments 1-21, wherein the treatment fluid is a fracturing fluid, remedial treatment fluid or stimulation fluid.

Embodiment 23 relates to the method of Embodiments 1-22, wherein the stimulation fluid is an acidizing fluid.

Embodiment 24 relates to the method of Embodiments 1-23, wherein the placing of the treatment fluid in the subterranean formation comprises fracturing at least part of the subterranean formation to form at least one subterranean fracture.

Embodiment 25 relates to the method of Embodiments 1-24, wherein the treatment fluid further comprises a proppant, a resin-coated proppant, or a combination thereof.

Embodiment 26 relates to a system configured to perform the method of Embodiments 1-25, the system comprising: the treatment fluid; and a drillstring disposed in a wellbore, the drillstring comprising a drill bit at a subterranean end of the drillstring.

Embodiment 27 relates to the system of Embodiment 26, wherein the system comprises an annulus between the drillstring and the wellbore; and the system further comprises a pump configured to circulate the treatment fluid through the drill string.

Embodiment 28 relates to the system of Embodiment 27, further comprising a fluid processing unit configured to process the composition exiting the annulus to generate a cleaned composition for recirculation through the wellbore.

Embodiment 29 relates to the system of Embodiments 26-28, further comprising a tubular disposed in a wellbore; and a pump configured to pump the composition into the subterranean formation.

What is claimed is:

1. A method comprising:
   obtaining or providing a treatment fluid, wherein the treatment fluid is an acidizing fluid comprising an acid and a compound of the formula (III):

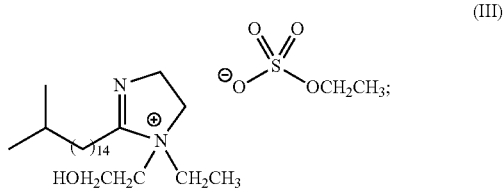

placing the treatment fluid in a subterranean formation via equipment comprising metal;
inhibiting corrosion of the metal in the presence of the acid with the compound, wherein the conditions comprise a temperature from about 100° F. to about 250° F.;
after the placing, contacting the acid with the subterranean formation so as to form spent acid such that the treatment fluid comprises spent acid after the placing; and
gelling the treatment fluid in the presence of the spent acid with the compound, wherein the conditions comprise a temperature from about 100° F. to about 250° F.

2. The method of claim 1, wherein the treatment fluid has a viscosity of about 30 cP to about 150 cP at a shear rate of about 20 s$^{-1}$ to about 200 s$^{-1}$ at about 225° F. in the presence of the spent acid.

3. The method of claim 1, wherein $R_1$ and $R_2$ are each, independently, an optionally substituted $C_1$-$C_5$ hydrocarbyl group; $R_3$ is a $C_{15}$-$C_{25}$ hydrocarbyl group; and $R_4$-$R_7$ are each, independently, H or an optionally substituted $C_1$-$C_{10}$ hydrocarbyl group.

4. The method of claim 1, wherein $R_1$ and $R_2$ are each, independently, an optionally substituted $C_1$-$C_5$ hydrocarbyl group; $R_3$ is a $C_{15}$-$C_{25}$ hydrocarbyl group; and $R_4$-$R_7$ are each H.

5. The method of claim 1, wherein $R_1$ is an unsubstituted $C_1$-$C_5$ hydrocarbyl group; $R_2$ is a hydroxyl-substituted $C_1$-$C_5$ hydrocarbyl group; $R_3$ is a $C_{15}$-$C_{25}$ hydrocarbyl group; $R_4$-$R_7$ are each, independently, an H or an optionally substituted $C_1$-$C_{10}$ hydrocarbyl group.

6. The method of claim 1, wherein $Y^-$ is an organic counterion.

7. The method of claim 6, wherein the organic counterion is selected from the group consisting of an alkoxide, a carboxylate, an organic sulfate, and an organic sulfonate.

8. The method of claim 6, wherein the organic counterion is an organic sulfate.

9. The method of claim 6, wherein the organic counterion is an organic sulfate of the formula $R_8OSO_3^-$, wherein $R_8$ represents a $C_1$-$C_{10}$ hydrocarbyl group.

10. The method of claim 1, wherein the treatment fluid exhibits viscoelastic behavior.

11. The method of claim 1, wherein the treatment fluid further comprises a gelling agent in addition to the compound and a crosslinking agent.

12. The method of claim 11, wherein the gelling agent comprises alginate, chitosan, curdlan, dextran, emulsan, a galactoglucopolysaccharide, gellan, glucuronan, N-acetyl-heparosan, hyaluronic acid, indicant, kefiran, lentinan, levan, mauran, pullulan, scleroglucan, schizophyllan, stewartan, succinoglycan, xanthan gum, xylane, welan, starch, tamarind, tragacanth, guar gum, derivatized guar, gum ghatti, gum arabic, locust bean gum, diutan gum, cellulose, hydroxyethylcellulose, hemicellulose, carboxymethyl cellulose, hydroxyethyl cellulose, carboxymethyl hydroxyethyl cellulose, hydroxypropyl cellulose, methyl hydroxyl ethyl cellulose, guar, hydroxypropyl guar, carboxy methyl guar, carboxymethyl hydroxylpropyl guar or combinations thereof.

13. The method of claim 11, wherein the crosslinking agent comprises boric acid, disodium octaborate tetrahydrate, sodium diborate, pentaborates, ulexite, colemanite, zirconium oxychloride, chelates of zirconium, derivatives thereof or combinations thereof.

14. The method of claim 1, wherein the treatment fluid further comprises a corrosion inhibitor in addition to the compound.

15. The method of claim 14, wherein the treatment fluid further comprises a corrosion inhibitor intensifier composition.

16. The method of claim 1, wherein the obtaining or providing of the composition occurs above-surface.

17. The method of claim 1, wherein the obtaining or providing of the composition occurs downhole.

18. The method of claim 1, wherein the method is a method of drilling the subterranean formation.

19. The method of claim 1, wherein the placing of the treatment fluid in the subterranean formation comprises fracturing at least part of the subterranean formation to form at least one subterranean fracture.

20. The method of claim 1, wherein the treatment fluid further comprises a proppant, a resin-coated proppant, or a combination thereof.

21. A system configured to perform the method of claim 1, the system comprising:
the treatment fluid; and
the equipment, wherein the equipment comprises a drillstring disposed in a wellbore, the drillstring comprising a drill bit at a subterranean end of the drillstring.

22. The system of claim 21, wherein the system comprises an annulus between the drillstring and the wellbore; and the system further comprises a pump configured to circulate the treatment fluid through the drill string.

23. The system of claim 22, further comprising a fluid processing unit configured to process the composition exiting the annulus to generate a cleaned composition for recirculation through the wellbore.

24. The system of claim 21, further comprising
a tubular disposed in the wellbore; and
a pump configured to pump the composition into the subterranean formation.

25. The method according to claim 1, wherein the method further comprises diverting another fluid in the subterranean formation with the treatment fluid.

26. The method according to claim 1, wherein the method further comprises matrix acidizing the subterranean formation with the treatment fluid.

27. The method according to claim 1, wherein the method further comprises acid fracturing the subterranean formation with the treatment fluid.

28. The method according to claim 1, wherein the treatment fluid excludes additional corrosion inhibitors.

29. The method according to claim 1, wherein the spent acid comprises a component selected from the group consisting of $CaCO_3$, $CaMg(CO_3)_2$, and combinations thereof.

* * * * *